United States Patent [19]

Thomas

[11] 4,405,797

[45] Sep. 20, 1983

[54] PROCESS FOR PREPARING SPECTINOMYCIN ANALOGS: N-DEMETHYLATION OF SPECTINOMYCIN OR ITS ANALOGS AND REALKYLATION OF THE INTERMEDIATES

[75] Inventor: Richard C. Thomas, Oshtemo Township, Kalamazoo County, Mich.

[73] Assignee: The Upjohn Company, Kalamazoo, Mich.

[21] Appl. No.: 312,035

[22] Filed: Oct. 16, 1981

[51] Int. Cl.[3] .............................................. C07D 323/04
[52] U.S. Cl. ..................................................... 549/361
[58] Field of Search ....................... 260/340.3; 549/361

[56] References Cited

U.S. PATENT DOCUMENTS 3,583,972  6/1971  Birkenmeyer et al. ................ 536/11
4,264,776  4/1981  Hershman et al. ................... 564/384

OTHER PUBLICATIONS

Birkenmeyer et al, Tetrahedron Letters, No. 58, pp. 5049–5051, (1970).
Rosenbrook et al, ACS Symposium Series, No. 125, pp. 133–144, (1980).

Primary Examiner—Ethel G. Love
Attorney, Agent, or Firm—Joan Thierstein

[57] ABSTRACT

This invention is a novel chemical process particularly concerned with N-dealkylation of secondary amines as found in amino-cylitols of which spectinomycin is an example. Separation and further alkylation also comprise the present invention process.

8 Claims, No Drawings

PROCESS FOR PREPARING SPECTINOMYCIN ANALOGS: N-DEMETHYLATION OF SPECTINOMYCIN OR ITS ANALOGS AND REALKYLATION OF THE INTERMEDIATES

DESCRIPTION

Background of the Invention

Tertiary amines possessing an N-alkyl group are dealkylated in the presence of oxygen and a catalyst in polar solvents in U.S. Pat. No. 3,583,972 and Birkenmeyer et al. "LINCOMYCIN. XIII. N-DEALKYLATION OF LINCOMYCIN AND ITS ANALOGS", Tetrahedron Letters No. 58, pp. 5049–5051, 1970. The compounds prepared by the process of this invention are disclosed in copending U.S. application Ser. No. 150,530, filed May 16, 1980, now U.S. Pat. No. 4,351,771, which is a continuation-in-part of U.S. application Ser. No. 020,172, now abandoned. Additionally, N-demethylated spectinomycins are disclosed by Rosenbrook et al., ACS Symposium Series No. 125, pp. 133-144 (1980). However, the reference claims that these compounds were totally inactive. Furthermore, no experimental details or structures are revealed therein. The disclosure that the N-demethylated spectinomycin compounds are bio-inactive is contrary to the finding of the compounds prepared by the present invention. In other words, it appears that Rosenbrook et al. have not isolated the materials. Therefore, the prior art does not teach the dealkylation in the presence of oxygen and a catalyst in polar solvents conducted on a secondary amine of the hydrochloride salt of spectinomycin or its presently known analogs. Processes modifying the actinamine ring of spectinomycin or its analogs is surprising in view of the high degree of functionality present in the molecule, the water-solubility of spectinomycin or its analogs, and the lability of the masked α-diketone systems at carbons 2' and 3' (see Formula I for carbon numbering). Furthermore, exposure of spectinomycin or its analogs to mild alkaline conditions results in rearrangement yielding inactive actinospectinoic acid type molecules having the structure shown by Formula IV. Such rearrangement is of great importance since the C-3' carbonyl is required for optimal activity in an aminocyclitol antibiotic of which spectinomycin (Formula Ia) is a unique structure. Reduction of the C-3' ketone to give dihydrospectinomycins improves stability, but greatly reduces bioactivity. Furthermore, reoxidation of such dihydro compounds is difficult.

FIELD OF THE INVENTION

This invention is a novel chemical process particularly concerned with N-dealkylation of secondary amines as found in aminocyclitols having the Formula I wherein R and R' are the same or different and are alkyl of from $C_1$ to $C_8$, inclusive, lower alkenyl, lower haloalkyl or lower aminoalkyl, lower alkynyl or —OX and —$(CH_2)_n$—OX; wherein X is lower alkyl, lower alkenyl, benzyl and acyl.

The process comprises treating with oxygen an aminocyclitol compound having Formula I often in the form of its acid addition salts, e.g. hydrochloric acid salt, in the presence of a catalyst, e.g. platinum, palladium, ruthenium, rhodium and other nobel metals as well as nickel in a polar solvent to obtain the corresponding N-dealkylamino-cyclitol of configuration II wherein $R_1$ and $R_2$ may be the same or different such that both $R_1$ and $R_2$ may be hydrogen, a mixture of compounds such that when $R_1$ is hydrogen then $R_2$ is methyl and when $R_1$ is methyl then $R_2$ is hydrogen (for ease of notation hereafter IIa is $R_1$ and $R_2$=hydrogen, IIb is a mixture of $R_1$=hydrogen and $R_2$=methyl, and $R_1$=methyl and $R_2$=hydrogen), and R and R' are as defined for Formula I above. The oxygen may be pure oxygen or diluted oxygen, e.g. air (see Scheme A or Scheme B, Step 1). Separation and alkylation to prepare compounds of formula III wherein $R_3$ and $R_4$ are as defined hereafter. further comprise the present invention (see Scheme B, steps 2 and 3a or 3b).

DESCRIPTION OF PREFERRED EMBODIMENT

The process of the present invention, in its narrower aspects, can be illustratively represented by Scheme B wherein $R_1$ and $R_2$ may be the same or different, and are as defined above, and by Schemes C and D wherein $R_3$ and $R_4$ are the same or different such that $R_3$ and $R_4$ are both —$CH_2CH_3$, or a mixture of compounds such that in one compound when $R_3$ is —$CH_3$ then $R_4$ is —$CH_2CH_3$, and in the other when $R_4$ is —$CH_3$ then $R_3$ is —$CH_2CH_3$.

Thus, the novel method of N-dealkylation is useful for the preparation of many products from aminocyclitol compounds such as spectinomycin and its analogs. For example, the nitrogen atom of the N-demethylated compounds may then be functionalized by reductive alkylation. Thus, the novel method provides constraints required by such alkylation of N-demethylated aminocyclitols. It provides for the use of aqueous solution for solubility reasons and acid pH due to the lability of the sugar rind under basic conditions. Furthermore, the present invention unexpectedly avoids the unwanted concomitant reduction of the highly electrophilic C-3' carbonyl. Finally, the present invention controls the alkylation to give only secondary amine products, avoiding N,N-dialkylation to yield the corresponding tertiary amines. For this purpose, the reductive alkylation using sodium cyanoborohydride as the reducing agent as described by Borch et al., J. Am. Chem. Soc., 93, pp. 2897–2904 (1971) is used.

In the foregoing designation of variables, "alkyl of $C_1$ through $C_8$" means methyl, ethyl, propyl, isopropyl, butyl, pentyl, hexyl, heptyl, octyl and isomers thereof.

"Alkyl of from one through four carbons" or "lower alkyl" means methyl, ethyl, propyl, isopropyl, butyl, sec-butyl, isobutyl and tert-butyl.

"Lower alkenyl" means ethylidene, propylidene, butylidene, pentylidene, hexylidene, heptylidene, octylidene and the isomeric forms thereof.

"Lower haloalkyl" means —$(CH_2)_n$—halo and isomeric forms thereof wherein n is from one through eight and "—$(CH_2)_n$" includes straight chain alkyls and isomers thereof. The group contains one to three halo substituents. "Halo" means fluoro, chloro, bromo and iodo. "Acyl" means formyl, acetyl, propionyl, butyryl, pentanoyl and isomeric forms thereof.

"Lower aminoalkyl" means

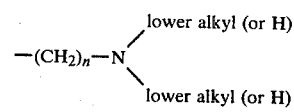

wherein n is from one through eight.

"Lower alkynyl" means ethynyl, propynyl, butynyl, pentynyl, hexynyl, heptynyl, octynyl and isomeric forms thereof.

For the specific field of spectinomycin and its analogs subjected to the above processes antibiotic compounds are prepared. Comparisons among spectinomycin, mono-N-demethylspectinomycin, mono-N-demethyl-mono-N-ethylspectinomycin, N,N'-didemethylspectinomycin and N,N'-didemethyl-N,N'-diethylspectinomycin (see Scheme A) follow.

| | | Minimum Inhibitory Concentration (Micrograms/Milliliter) In Vitro | | | | |
|---|---|---|---|---|---|---|
| Organism | UC# | Spectinomycin Ia | Mono-N—Demethyl-Spectinomycin IIb | Mono-N—Demethyl-Mono-N—Ethyl Spectinomycin IIIb | N,N'—Dimethyl-Spectinomycin IIa | N,N'—Didemethyl N,N'—Diethyl Spectinomycin IIIa |
| S. aureus | 76 | 7.8 | 15.6 | 31.2 | 250 | 500 |
| S. faecalis | 694 | 31.2–62.5 | 125 | 500 | >1000 | >1000 |
| E. coli | 45 | 3.9–7.8 | 62.5 | 62.5 | >1000 | 1000 |
| K. pneumoniae | 58 | 2.0–3.9 | 15.6 | 3.9 | 125 | 31.2 |
| Ps. aeruginosa | 95 | 31.2 | 62.5 | 31.2 | 250 | 1000 |
| P. vulgaris | 93 | 7.8–15.6 | 15.6 | 7.8 | 125 | 125 |
| P. mirabilis | 6671 | 3.9–7.8 | 15.6 | 15.6 | 1000 | 62.5 |
| S. flexneri | 143 | 3.9–7.8 | 15.6 | 15.6 | 250 | 31.2 |
| S. typhi | 215 | 3.9–7.8 | 62.5 | 125 | >1000 | 1000 |
| S. marcescens | 131 | 3.9–7.8 | 3.9 | 7.8 | 31.2 | 62.5 |
| S. Schottmuelleri | 126 | 7.8 | — | 62.5 | — | >1000 |
| P. stuartii | 6570 | 1000 | — | >500 | — | >1000 |

Thus, spectinomycin analogs bearing modified amino cyclitols show corresponding antibacterial activity and formulation of the compounds II and III prepared by the processes of the present invention are as fully disclosed in U.S. Pat. No. 3,234,092, and the copending application Ser. No. 150,530 noted above.

In carrying out the process of this invention, a selected substrate such as one of the spectinomycin compounds of Formula I as mentioned above, often in the form of its hydrochloride or other acid addition salts, is dissolved in water or in mixtures of water with a water miscible, organic solvent unreactive in this reaction. Organic solvents to be used with water for this reaction are tertiary butyl alcohol, tetrahydrofuran, acetone or the like. The solution is then treated with oxygen (e.g. gas, air) in the presence of a catalyst selected from the group consisting of noble metals and Raney nickel. The noble metals used for this reaction are platinum, palladium, rhodium and ruthenium. Between 0.25–10 parts by weight of catalyst is used per part of substrate. The reaction is carried out between 0° and 100° C., preferably 50°–60° C.

In the preferred embodiment of this reaction, the substrate in solution with 0.5 to 1.5 parts by weight of platinum catalyst to 1 part of substrate is treated with oxygen gas from 1 to 24 hours (about 50°–60° C.). If the conversion is incomplete (as shown, for example, by thin layer chromatography of an aliquot), the above treatment is repeated with fresh catalyst until the starting material has been converted. At the termination of the reaction, the product is found to include compounds wherein $R_1$ and $R_2$ are both hydrogen or a mixture of compounds wherein $R_1$ is hydrogen, $R_2$ is methyl, and $R_1$ is methyl, $R_2$ is hydrogen.

In other words, there appears to be no kinetic preference for selective removal of the either of the methyl groups and the mono-demethylated spectinomycin are isolated as a 1:1 mixture.

Competitive oxidation of the hydroxyl groups and the cleavage of the ring carbon nitrogen bonds are surprisingly not serious problems. Reaction for extended periods at elevated temperatures, however, does result in a production of small amounts of colored byproducts with a characteristic phenolic odor suggesting that some oxidation does occur on the actinamine ring.

The base lability of spectinomycin causes problems in separating the product mixture into its component parts. The facile rearrangement of spectinomycin free base dictates that separation be done on salts or N-protected derivatives. Purification of the hydrogen chloride salts via ion exchange, carbon, cellulose or silica gel chromatography, are not advisable. Purification is preferably achieved by conversion of the mixture to N-protected derivatives such as the alkyloxycarbonyl, isopropoxycarbonyl, isobutyloxycarbonyl, cyclopentyloxycarbonyl, cyclohexyloxycarbonyl, $\beta,\beta,\beta$-trichloroethoxycarbonyl, 4-methoxybenzyloxycarbonyl derivatives, or preferably either the benzyloxycarbonyl or tert-butoxycarbonyl (t-BOC) derivatives. Such conversion is well-known in the art and may be accomplished as described by R. A. Boissonas, "Selectively Removeable Amino Protective Group Used in the Synthesis of Peptides," in *Advances in Organic Chemistry*, 3:159–190 (1963). Information on the use of the tert-butyloxycarbonyl group to block amine is also described in ALDRICH Technical Information Bulletin entitled "BOC-ON" (September, 1976). See Scheme B step 2 (separation). These compounds are then readily separated by rapid chromatography on silica gel. However, isomers of the isomeric mixture of mono-N-demethylspectinomycins are not separated by this method but only isolated as a mixture free of residual spectinomycin and the didemethyl analogs. The use of benzyloxycarbonyl or tert-butoxycarbonyl circumvents the problem of competing reduction of the C-3' carbonyl present in the usual deprotection of nitrogen-protected spectinomycins and therefore is preferred.

Reductive alkylation (Schemes C and D) is accomplished by a treatment of either mixtures of mono-demethylated aminocyclitols having Formula IIb or didemethylated aminocyclitols of Formula IIa with an excess of ethanal and a reducing agent such as hydrogen and a catalyst such as nickel, rhodium, ruthenium, palladium, platinum either as the pure metal, or the metal on a support such as charcoal, barium sulfate or alumina or preferably with sodium cyanoborohydride (NaBH$_3$CN) at a pH of 3 to 6, preferably 4 which results in the rapid consumption of the starting material and formation of the desired nitrogen alkylated analogs. Purification is accomplished by applying the crude reaction product to a synthetic carbon resin Ambersorb XE-348 column.

The resin is subsequently washed with deionized water to remove the salts. Elution with aqueous acetone completes the purification process.

Acid addition salts of the invention compounds can be made by neutralizing the compound with an appropriate acid to below about pH 7.0, and advantageously about pH 2 to pH 6. Suitable acids for this purpose include tartaric, glucuronic, lactic, hydrochloric, sulfuric, phosphoric, sulfamic, hydrobromic, and the like. Acid salts of spectinomycin analogs can be used for the same biological purposes as the parent compound.

The following examples of dealkylation, separation and reductive alkylation of spectinomycin Ia are indicative of the invention process and are not to be construed as limitative. Those skilled in the art will readily recognize appropriate variations from the procedure both as to variations on the starting material Ia as well as reaction conditions and techniques. These examples indicate the best mode presently known to the inventor.

EXAMPLE 1

Preparation of an isomeric mixture of Mono-N-demethyl-spectinomycin IIb and N,N'-didemethylspectinomycin IIa (see Scheme B)

Step (1): Preparation of II a/b wherein (a) is a compound wherein $R_1$ and $R_2$ are H, and (b) is a mixture of compounds wherein $R_1$ is H, $R_2$ is $CH_3$ and $R_1$ is $CH_3$, $R_2$ is H Platinum oxide (6.0 g, 26.4 mmol) is reduced in 20 ml of deionized water for 3 hours at 40 pounds per square inch of hydrogen on the Parr hydrogenation apparatus. Spectinomycin dihydrochloride pentahydrate (20.0 g, 40.4 mmol) is dissolved in 200 ml of water, the platinum catalyst is added and the solution is warmed to 60° C. The suspension is rapidly stirred and oxygen gas is passed through the solution via a gas dispersion tube for 17 hrs. The catalyst is removed by filtration and an aliquot is lyophilized for analysis. The silylated sample (1:1 dimethylformamide-hexamethyldisilazane, 50° C., 30 minutes) shows three major peaks by gas chromatography (3% OV-17, 80 cm, 150°–250° C. @ 5°/min.) corresponding to spectinomycin Ia, the isomeric monodemethylated compounds IIb, and the didemethylated IIa in a ratio of 25/52/14, respectively.

Step (2): Separation of IIa and IIb from the product mixture of step (1) by preparing IIa (protected), IIb (protected)

The volume is reduced to ~100 ml and the solution is cooled to 0° C. Sodium bicarbonate, $NaHCO_3$, (9.0 g, 107 mmol) is added, the mixture is stirred 10 minutes and a solution of 19.2 g (88.0 mmol) of di-tert-butyldicarbonate (t-BOC) in 120 ml of tert-butanol is added. The mixture is warmed to room temperature and stirred 21.5 hours. The butanol is removed in vacuo, 100 ml of water is added and the mixture is extracted with 500 ml of ethylacetate. The ethylacetate is washed with 100 ml of water, 100 ml of brine, dried over $MgSO_4$ and concentrated in vacuo to give 16.8 g of yellow glass. Chromatography on 600 g of silica gel (methanol/-chloroform gradient 2→4%) gave the following fractions, pooled on the basis of TLC (10% methanol/-chloroform): 0.36 g of Ia (protected); 1.94 g of Ia (protected) and the mixture of isomers IIb (protected); 3.14 g of the mixtures of isomers IIb; 3.48 g of a mixture of IIa and the mixture of isomers IIb (protected); 1.49 g of IIa (protected). The isomeric mono-demethyl compounds IIb (protected) are not resolved by this method.

For the isomeric mixture of N,N'-di-tertbutoxycarbonyl-mono-N-demethylspectinomycin IIb (protected):
CMR $(CD_3COCD_3)\delta 191.5, 157, 97.4, 97.1, 92.0, 79.6, 79.2, 74.8, 74.6, 72.7, 71.1, 70.0, 69.2, 68.2, 67.0, 66.0, 60.1, 57.1, 56.8, 54.3, 45.6, 28.9, 28.6, 21.6$; IR $(CHCl_3)$ 3500, 3000, 1730, 1680, 1490, 1440, 1380, 1350, 1240, 1150, 1120, 1050, 870 cm$^{-1}$; $[\alpha]_D$-12° (C, 0.916, $CHCl_3$); mp 153°–180° decomposition;
MS (for tristrimethylsilylether) $C_{32}H_{62}N_2O_{11}Si_3$ requires 734.3661.
Found: 734.3665.

For N,N'-di-tertbutoxycarbonyl-N,N'didemethyl-spectinomycin IIa (protected):
CMR $(CD_3COCD_3)\delta 156.7, 97.14, 91.9, 79.1, 74.1, 71.1, 69.3, 68.2, 68.0, 56.7, 53.4, 45.7, 28.6, 21.6$, IR $(CHCl_3)$ 3500, 3000, 1690, 1500, 1445, 1380, 1360, 1240, 1160, 1130, 1060, 1040, 975, 870 cm$^{-1}$; $[\alpha]_D$-15° (C, 0.893, $CHCl_3$); mp 160°–180° decomposition;
MS (for tristrimethylsilylether) $C_{31}H_{60}N_2O_{11}Si_3$ requires 720.3505.
Found: 720.3481.

Step (3a): Preparation of N,N'-didemethylspectinomycin dihydrochloride IIa by deprotecting IIa (protected)
N,N'-di-tertbutoxycarbonyl-N,N'-didemethylspectinomycin IIa (protected) (1.50 g, 3.0 mmol) from Step (2) above is dissolved in 300 ml of methylene dichloride and cooled with an ice bath. Gaseous hydrogen chloride is bubbled through the solution for 60 seconds and the mixture is stirred 1 hour at 0°. Removal of solvent in vacuo gives 1.14 g (3.0 mmol, 100%) of product IIa as a white solid; mp 186°–210° decomposition);
CMR $(D_2O, CH_3CN$ int. std.$)\delta 94.6, 92.7, 71.0, 69.3, 67.2, 66.8, 67.0, 55.6, 52.6, 42.6, 20.8$; IR (KBr) 3400, 2900, 1600, 1500, 1370, 1150, 1050, 1020, 960 cm$^{-1}$; $[\alpha]_D$+15° (C, 0.726, $H_2O$);
MS (for pentakistrimethylsilyl ether) $C_{27}H_{60}N_2O_7Si_5$ requires 664.3247.
Found: 664.3294.

Step (3b): Preparation of the isomeric mixture of Mono-N-demethylspectinomycin dihydrochlorides IIb by deprotecting IIb (protected)
A solution of 200 mg (0.39 mmol) of the IIb (protected) mixture from Step (2) above in 40 ml of methylene dichloride is cooled with an ice bath and gaseous hydrogen chloride is passed into the solution for 30 seconds. The mixture is stirred 40 minutes at 0° and concentrated in vacuo to give 150 mg (0.38 mmol, 98%) of the mixture of IIb as a white powder; mp 186°–210° (decomposition);
CMR $(D_2O, CH_3CN$ int. std.$)\delta 94.5, 92.7, 70.8, 69.3, 67.0, 66.7, 63.2, 62.5, 59.5, 55.6, 52.6, 42.5, 31.9, 31.4, 20.7$; IR (KBr) 3500, 3000, 1750, 1600, 1530, 1460, 1380, 1050 cm$^{-1}$; $[\alpha]_D$+8 (C, 0.93, $H_2O$);
MS (for pentakistrimethylsilyl ether) $C_{28}H_{62}N_2O_7Si_5$ requires 678.3403.
Found: 678.3420.

Variation of Step (1)

A total of 12 g of platinum oxide is prereduced as described above. Spectinomycin dihydrochloride pentahydrate (20.0 g, 40.4 mmol) is dissolved in 250 ml of deionized water and heated to 50° with rapid stirring. Oxygen is bubbled through the solution and the catalyst is added in portions over five days. After four additional days, the catalyst is removed by filtration, the filtrate is treated with 2 g of Darco decolorizing carbon, filtered and lyophilized to afford 15.2 g of pale yellow solid. Analysis by gas chromatography as above shows the presence of the isomeric monodemethylated compounds IIb and the fully demethylated product IIa in a ratio of 19 to 43. A new unidentified peak of longer retention time appears after prolonged reaction.

EXAMPLE 2

Preparation of N,N'-didemethyl-N,N'-diethylspectinomycin dihydrochloride IIIa (see Scheme C wherein $R_3$ and $R_4$ are $CH_2CH_3$)

N,N'-didemethylspectinomycin dihydrochloride IIa from Step (3a) above (230 mg, 0.61 mmol) and acetaldehyde (0.5 ml, 8.9 mmol) are dissolved in 2 ml of water and a drop of dilute methanolic methyl orange indicator is added giving a pink solution. A solution of 25.5 mg (0.41 mmol, 1.22 mmol of $H^-$) of sodium cyanoborohydride in 1 ml of water is added all at once, causing the color to turn to yellow. Aqueous 1 N hydrogen chloride is added dropwise to maintain the pink color, and the mixture is stirred one hour at room temperature. The excess acetaldehyde is removed in vacuo and the aqueous solution of the crude product is loaded onto an 80 ml bed of Ambersorb XE-348. The column is washed with 200 ml of water and then 0.004 M hydrogen chloride in 50% aqueous acetone. The third and fourth 25 ml fractions of the aqueous acetone eluent are pooled, concentrated, adjusted to pH 4 with hydrogen chloride and lyophilized to afford 30 mg (0.30 mmol, 50%) of IIIa as a white solid; mp 220°–235° (decomposition).

$^{13}C$ NMR ($D_2O$)δ94.4, 92.7, 70.8, 69.2, 66.9, 66.5, 61.2, 60.6, 57.8, 42.4, 41.9, 41.6, 20.7, 11.4; $[\alpha]_D + 5°$ (C, 0.874, $H_2O$); ms m/e (tetra TMS) 576, 561, 273, 217, 201, 185, 159, 73.

Exact mass calc'd. for: $C_{25}H_{52}Si_3N_2O_7$;576.3082. Found: 576.3107.

EXAMPLE 3

Preparation of mono-N-demethyl-mono-N-ethylspectinomycin dihydrochloride IIIb (see Scheme D) wherein the product is a mixture of such that in one compound of the mixture $R_3$ is $CH_3$ and $R_4$ is $CH_2CH_3$ and in another compound of the mixture $R_3$ is $CH_2CH_3$ and $R_4$ is $CH_3$ To a solution of 200 mg (0.52 mmol) of the mixture of isomers mono-N-demethylspectinomycin dihydrochloride IIb from Step (3b) above and 0.4 ml (7.2 mmol) of acetaldehyde in 1 ml of $H_2O$ is added a drop of dilute methanolic methyl orange indicator, giving a pink solution. A solution of 10.7 mg (0.17 mmol) of sodium cyanoborohydride, $NaBH_3CN$, in 1.07 ml of $H_2O$ is added followed by dropwise addition of 1 N hydrogen chloride to maintain the pink color. The mixture is stirred 30 minutes at room temperature, stored in the freezer overnight and then lyophilized. Analysis by $^{13}C$ NMR and GC-MS (trimethylsilyl derivative) show the product to be a mixture of the isomeric N-methyl-N'-ethyl spectinomycin dihydrochloride IIIb.

The crude product IIIb is dissolved in 2 ml of deionized water and 134 mg (1.6 mmol) of sodium bicarbonate is added (final pH=7). A solution of 348 mg (1.6 mmol) of di-tert butyldicarbonate in 2 ml of tert-butyl alcohol is added and the mixture is stirred 22 hours at room temperature. The mixture is added to 35 ml of ethyl acetate and 10 ml of water,° the layers are separated and the organics are dried with brine and $MgSO_4$. Removal of solvent gives 150 mg of white solid. The material is chromatographed on a 1×24 cm silica gel column (230–400 mesh) with 1% methanol/chloroform. The separation is poor and only 50 mg of partially purified material is recovered. Rechromatography with chloroform affords only 15 mg of a white solid.

This solid tert-butoxycarbonyl derivative is dissolved in 3 ml of methylene dichloride, cooled to 0° and treated with hydrogen chloride gas for 20 seconds. The mixture is stirred 45 minutes at 0° and concentrated in vacuo to give a white solid. Analysis by $^{13}C$ NMR and GC-MS revealed that this purification process separates out one of the isomeric N-methyl-N'-ethylspectinomycins.

$^{13}C$ NMR ($D_2O$)δ94.68, 94.62, 92.6, 71.0, 69.5, 67.1, 66.7, 61.0, 60.8, 59.7, 42.6, 41.9, 31.4, 20.8, 11.5; GC-MS m/e 562, 561, 545, 200, 184, 171, 159, 145.

FORMULAE

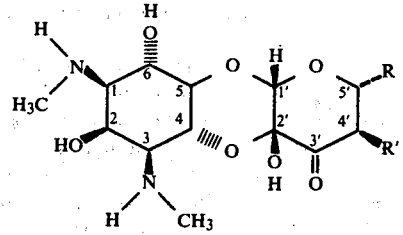

I

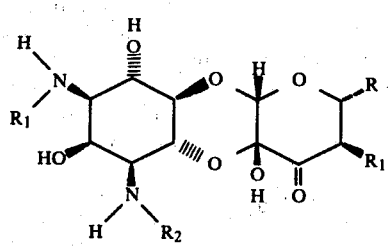

II

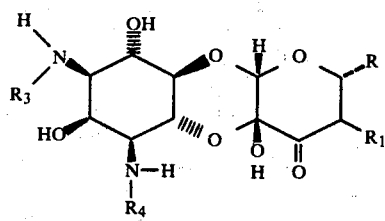

III

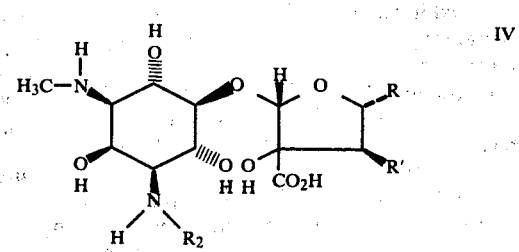

IV

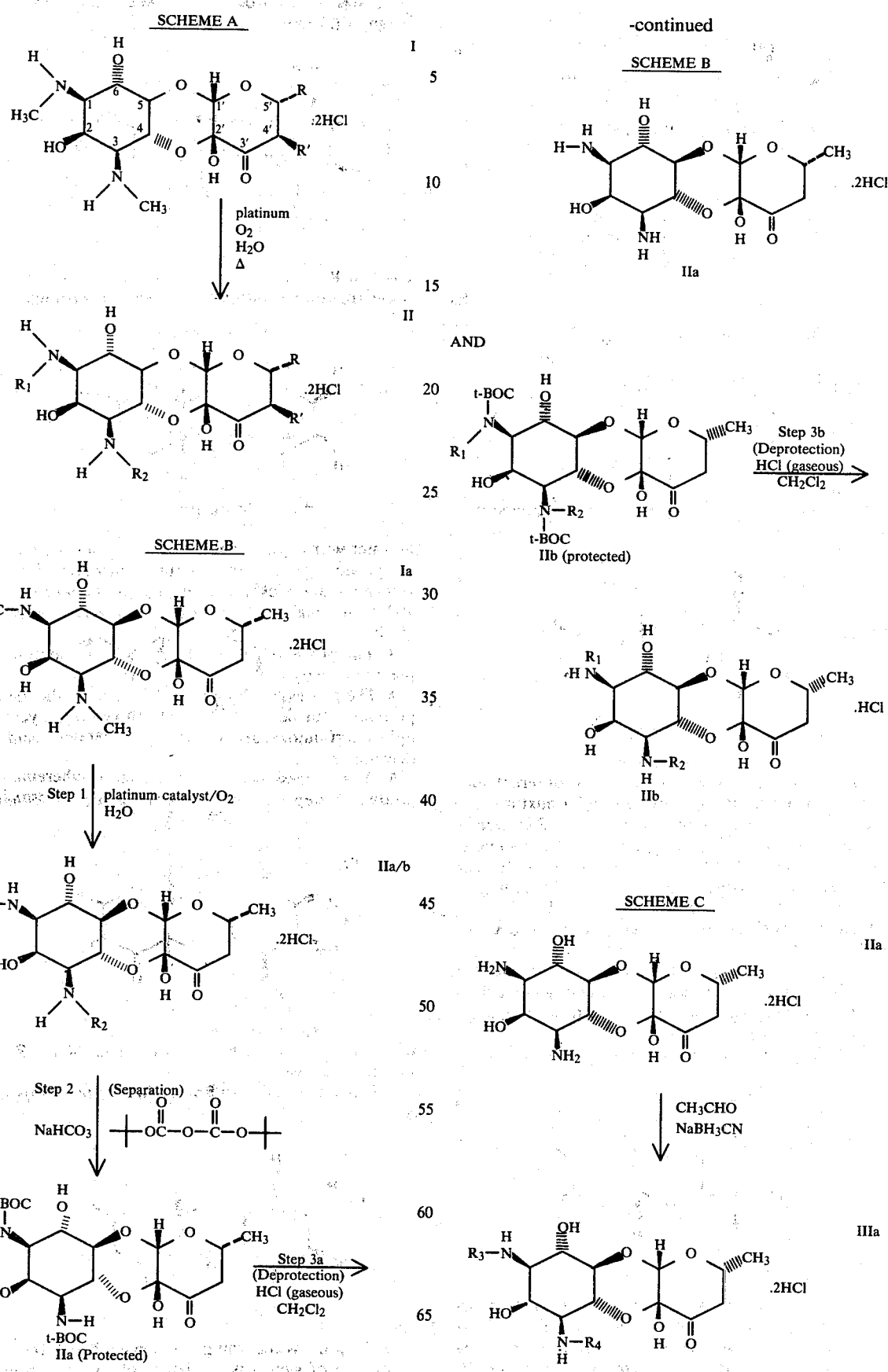

SCHEME D

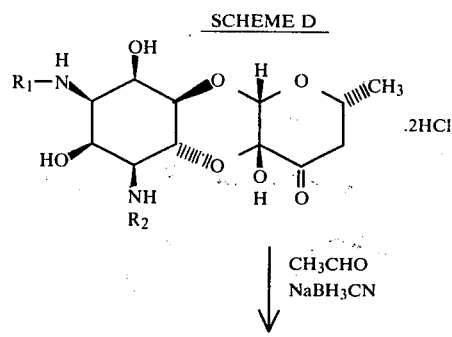

↓ CH₃CHO
NaBH₃CN

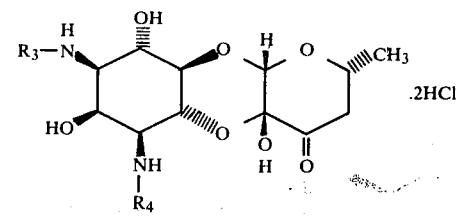

I claim:
1. A process for the preparation of a compound having the formula

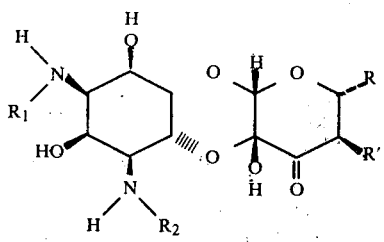

II wherein $R_1$ and $R_2$ may be the same or different such that $R_1$ and $R_2$ are both hydrogen, and a mixture such that in one compound of the mixture when $R_1$ is hydrogen then $R_2$ is methyl and that in another compound of the mixture when $R_2$ is hydrogen then $R_1$ is methyl, and R and R' are the same or different and are hydrogen, alkyl of from $C_1$ to $C_8$, inclusive, lower alkenyl, lower haloalkyl, lower aminoalkyl, lower alkynyl, —OX, and $(CH_2)n$—OX
  wherein n is an integer of from one to four, and X is lower alkyl, lower alkenyl, benzyl and acyl or pharmacologically acceptable acid addition salts thereof which comprises:
treating a compound having the formula

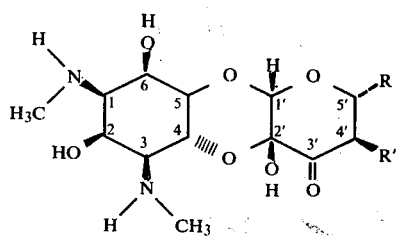

I wherein R and R' is as defined above, or the pharmacologically acceptable acid addition salts thereof in an aqueous solvent with oxygen in the presence of a catalyst at a temperature between 0° and 100° C. to obtain the product compound II.

2. A process according to claim 1 for the product having the formula

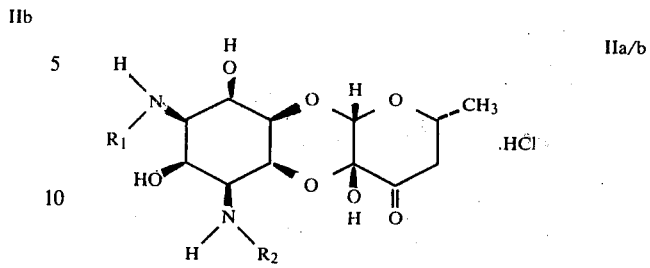

IIa/b wherein $R_1$ and $R_2$ are as defined above which comprises treating spectinomycin having the formula

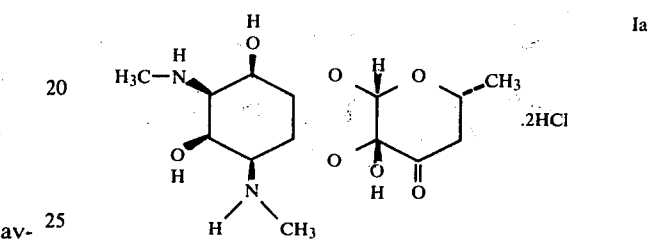

Ia in water with oxygen wherein the catalyst selected from the group consisting of platinum, palladium, rhodium, ruthenium and nickel at a temperature between 0° and 100° C. to obtain the corresponding product compound IIa/b.

3. The process of claim 2 in which the catalyst is a platinum catalyst.

4. The process according to claim 1 or 2 wherein the product is further (1) protected with benzyloxycarbonyl or tert-butoxycarbonyl then (2) separated and (3) deprotected.

5. The process according to claim 4 wherein the product of step 3 is the compound having the formula

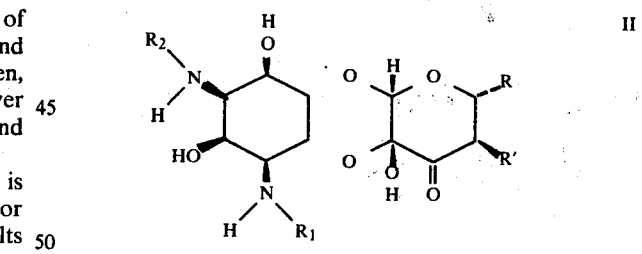

II wherein $R_1$ and $R_2$ are both hydrogen and R and R' are as defined above.

6. The process of claim 5 wherein the final compound is

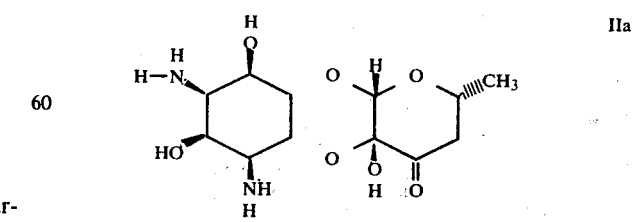

IIa

7. The process according to claim 4 wherein the final compound of step 3 is a mixture of two compounds having the formula

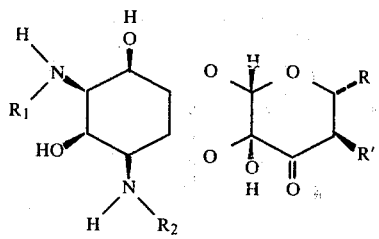
II
wherein one compound of the mixture is such that when $R_1$ is hydrogen then $R_2$ is methyl and another compound of the mixture is such that when $R_2$ is hydrogen then $R_1$ is methyl and R and R' are as defined above.
8. The process according to claim 7 wherein the final compound is a mixture having the formula
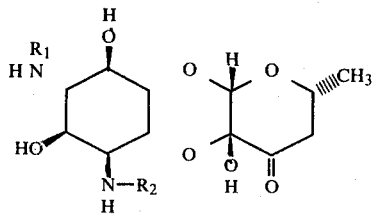
IIb
wherein $R_1$ and $R_2$ are as defined above.
* * * * *